(12) United States Patent
Schiff et al.

(10) Patent No.: US 12,377,209 B1
(45) Date of Patent: Aug. 5, 2025

(54) DEFORMABLE DRUG RESERVOIR FOR WEARABLE DRUG DELIVERY DEVICE

(71) Applicant: Fresenius Kabi Deutschland GmbH, Bad Homburg (DE)

(72) Inventors: David R. Schiff, Highland Park, NJ (US); Sharon D. West, Elkins Park, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 260 days.

(21) Appl. No.: 18/047,729

(22) Filed: Oct. 19, 2022

Related U.S. Application Data

(62) Division of application No. 17/246,116, filed on Apr. 30, 2021, now Pat. No. 11,504,470.

(51) Int. Cl.
*A61M 5/142* (2006.01)
*A61M 5/145* (2006.01)
*A61M 5/168* (2006.01)

(52) U.S. Cl.
CPC .... *A61M 5/14232* (2013.01); *A61M 5/14236* (2013.01); *A61M 5/14248* (2013.01);
(Continued)

(58) Field of Classification Search
CPC .... A61M 5/14244; A61M 2005/14208; A61M 5/142; A61M 5/14248; A61M 2202/0007;
(Continued)

(56) References Cited

U.S. PATENT DOCUMENTS 1,207,534 A * 12/1916 Gammeter ........... B65D 35/285
222/102
1,311,354 A * 7/1919 King ...................... B65D 35/28
222/101
(Continued)

FOREIGN PATENT DOCUMENTS

EP          2242034 A1    10/2010
WO     2018081234 A1     5/2018
(Continued)

OTHER PUBLICATIONS

Dexcom G6: Reusable Infiniflex Protective Overlay Guard Flexible Armor Case Cover. Etsy.com. https:..www.etsy.com/shop/OldsNewAgain?ref=simple-shop-header-name&listing_id=1081102727 (Year: 2021).
(Continued)

*Primary Examiner* — Quynh-Nhu H. Vu
(74) *Attorney, Agent, or Firm* — Cook Alex Ltd.

(57) ABSTRACT

A drug delivery device has a housing with an adhesive pad associated with the lower surface of the housing and configured to removably attach to a human body surface. A deformable drug reservoir is positioned within the housing and includes an outlet, with a needle fluidically connected to the drug reservoir and configured to define at least a portion of a fluid flow path between the drug reservoir and said human body surface. A delivery assembly is associated with the drug reservoir and includes a roller and a drive assembly, with the drive assembly being controlled by the controller during a drug delivery routine to move the roller from a first position to a second position so as to cause the roller to contact and deform the reservoir, thereby conveying a drug from the reservoir via the outlet.

19 Claims, 5 Drawing Sheets

(52) U.S. Cl.
CPC ...... *A61M 5/1454* (2013.01); *A61M 5/16881* (2013.01); *A61M 2005/14252* (2013.01); *A61M 2202/0007* (2013.01)

(58) Field of Classification Search
CPC .......... A61M 5/14232; A61M 5/14236; A61M 5/1454; A61M 5/148; A61M 5/1483; A61M 5/1486; A61M 5/152; A61M 5/16881; A61M 5/16804; B65D 35/285; B65D 35/28; B65D 35/00; B65D 35/30; B65D 47/286; B65D 47/28; B65D 47/283
See application file for complete search history.

(56) References Cited

U.S. PATENT DOCUMENTS

| | | | | |
|---|---|---|---|---|
| 2,168,080 A * | 8/1939 | Allen | ................... | B65D 35/28 222/498 |
| 2,712,400 A * | 7/1955 | Stauffer | ................. | B65D 35/28 222/96 |
| 3,151,616 A * | 10/1964 | Selfon | .................. | A61M 5/148 604/245 |
| 3,647,117 A * | 3/1972 | Hargest | ................. | A61M 5/148 222/100 |
| 3,670,926 A * | 6/1972 | Hill | ...................... | A61M 5/148 604/134 |
| 3,860,147 A * | 1/1975 | Vessio | ................... | B65D 35/285 222/105 |
| 4,019,655 A * | 4/1977 | Moeller | .................... | A47K 5/08 222/96 |
| 4,044,764 A * | 8/1977 | Szabo | ................... | A61M 5/148 222/102 |
| 4,072,149 A | 2/1978 | Tischlinger | | |
| 4,234,104 A * | 11/1980 | Apuzzo, Jr. | .......... | B65D 35/285 222/96 |
| 4,450,982 A * | 5/1984 | Ferreira | ................. | B65D 35/28 222/93 |
| 4,525,164 A * | 6/1985 | Loeb | ..................... | A61M 5/148 222/326 |
| 4,557,728 A * | 12/1985 | Sealfon | ................. | A61M 5/148 604/134 |
| 4,575,375 A * | 3/1986 | Kozam | ............... | A61M 3/0262 604/185 |
| 4,765,512 A * | 8/1988 | Bull, Jr. | ............... | B67D 1/0001 222/100 |
| 4,850,971 A * | 7/1989 | Colvin | .................. | A61M 5/148 222/100 |
| 4,970,502 A | 11/1990 | Kunikane et al. | | |
| 5,211,626 A * | 5/1993 | Frank | ..................... | G01F 1/7044 604/122 |
| 5,447,255 A * | 9/1995 | Smedley | .............. | B65D 35/285 222/102 |
| 5,875,929 A * | 3/1999 | Nguyen | ............... | B65D 35/285 222/102 |
| 6,620,134 B1 | 9/2003 | Trombley, III et al. | | |
| 6,669,668 B1* | 12/2003 | Kleeman | ............... | A61M 5/148 222/401 |
| 7,981,102 B2 | 7/2011 | Patel et al. | | |
| 8,285,328 B2 | 10/2012 | Caffey et al. | | |
| 8,652,108 B2* | 2/2014 | Basso | ................. | A61M 5/1483 604/207 |
| 9,452,255 B2 | 9/2016 | Tieck et al. | | |
| 2001/0016710 A1* | 8/2001 | Nason | ................... | A61M 5/148 604/153 |
| 2002/0169439 A1 | 11/2002 | Flaherty | | |
| 2003/0088238 A1 | 5/2003 | Poulsen et al. | | |
| 2003/0167036 A1 | 9/2003 | Flaherty | | |
| 2004/0068230 A1 | 4/2004 | Estes et al. | | |
| 2004/0116866 A1 | 6/2004 | Gorman et al. | | |
| 2004/0199123 A1 | 10/2004 | Nielsen | | |
| 2006/0111671 A1 | 5/2006 | Klippenstein | | |
| 2007/0290012 A1 | 12/2007 | Jackman | | |
| 2008/0091139 A1 | 4/2008 | Srinivasan et al. | | |
| 2008/0269657 A1 | 10/2008 | Brenneman et al. | | |
| 2009/0131860 A1 | 5/2009 | Nielsen | | |
| 2009/0156990 A1 | 6/2009 | Wenger et al. | | |
| 2010/0130931 A1* | 5/2010 | Yodfat | ................ | F04B 43/1269 604/151 |
| 2011/0060196 A1 | 3/2011 | Stafford | | |
| 2011/0178461 A1 | 7/2011 | Chong et al. | | |
| 2011/0196304 A1 | 8/2011 | Kramer et al. | | |
| 2011/0306941 A1* | 12/2011 | Chandrasekar | ..... | A61M 3/0254 604/262 |
| 2012/0010594 A1 | 1/2012 | Holt et al. | | |
| 2013/0006213 A1 | 1/2013 | Arnitz et al. | | |
| 2015/0119804 A1 | 4/2015 | Seeley et al. | | |
| 2015/0306307 A1 | 10/2015 | Cole et al. | | |
| 2015/0374919 A1 | 12/2015 | Gibson | | |
| 2016/0038689 A1 | 2/2016 | Lee et al. | | |
| 2016/0082182 A1 | 3/2016 | Gregory et al. | | |
| 2016/0175515 A1 | 6/2016 | McCullough | | |
| 2016/0199574 A1 | 7/2016 | Ring et al. | | |
| 2016/0220798 A1 | 8/2016 | Netzel et al. | | |
| 2016/0296704 A1 | 10/2016 | Gibson | | |
| 2016/0354555 A1 | 12/2016 | Gibson et al. | | |
| 2016/0374707 A1 | 12/2016 | Akagane | | |
| 2017/0119969 A1 | 5/2017 | McCullough et al. | | |
| 2017/0124284 A1 | 5/2017 | McCullough et al. | | |
| 2017/0147787 A1 | 5/2017 | Albrecht et al. | | |
| 2017/0182253 A1 | 6/2017 | Folk et al. | | |
| 2017/0312454 A1 | 11/2017 | Chattaraj et al. | | |
| 2017/0340837 A1 | 11/2017 | Nazzaro et al. | | |
| 2017/0361015 A1 | 12/2017 | McCullough | | |
| 2017/0368260 A1 | 12/2017 | McCullough et al. | | |
| 2018/0021508 A1 | 1/2018 | Destefano et al. | | |
| 2018/0028747 A1 | 2/2018 | Hanson et al. | | |
| 2018/0036476 A1 | 2/2018 | McCullough et al. | | |
| 2018/0085517 A1 | 3/2018 | Laurence et al. | | |
| 2018/0193554 A1 | 7/2018 | Meehan et al. | | |
| 2018/0193557 A1 | 7/2018 | Johnson et al. | | |
| 2018/0256823 A1 | 9/2018 | Nazzaro et al. | | |
| 2018/0272059 A1 | 9/2018 | Marbet et al. | | |
| 2018/0304014 A1 | 10/2018 | Knudsen et al. | | |
| 2019/0009019 A1 | 1/2019 | Shor et al. | | |
| 2019/0022306 A1 | 1/2019 | Gibson et al. | | |
| 2019/0050375 A1 | 2/2019 | Fitzgibbon et al. | | |
| 2019/0060562 A1 | 2/2019 | Olivas et al. | | |
| 2019/0083702 A1 | 3/2019 | Nekouzadeh et al. | | |
| 2019/0134296 A1 | 5/2019 | Barbedette et al. | | |
| 2019/0143043 A1 | 5/2019 | Coles et al. | | |
| 2019/0143047 A1 | 5/2019 | Jazayeri et al. | | |
| 2019/0151544 A1 | 5/2019 | Stonecipher | | |
| 2019/0167899 A1 | 6/2019 | Cabiri | | |
| 2019/0167908 A1 | 6/2019 | Fitzgibbon et al. | | |
| 2019/0192766 A1 | 6/2019 | Stonecipher | | |
| 2019/0247579 A1 | 8/2019 | Damestani et al. | | |
| 2019/0275241 A1 | 9/2019 | Ring et al. | | |
| 2019/0321544 A1 | 10/2019 | List | | |
| 2019/0328965 A1 | 10/2019 | Moberg | | |
| 2019/0365986 A1 | 12/2019 | Coiner et al. | | |
| 2019/0374707 A1 | 12/2019 | Damestani et al. | | |
| 2019/0381238 A1 | 12/2019 | Stonecipher et al. | | |
| 2020/0023122 A1 | 1/2020 | McCullough et al. | | |
| 2020/0086044 A1 | 3/2020 | Streit et al. | | |
| 2020/0164145 A1 | 5/2020 | Chang et al. | | |
| 2020/0164155 A1 | 5/2020 | Mojarrad et al. | | |
| 2020/0169439 A1 | 5/2020 | Kim et al. | | |
| 2020/0179609 A1 | 6/2020 | Tan-Malecki et al. | | |
| 2020/0197628 A1 | 6/2020 | McCullough et al. | | |
| 2020/0206429 A1 | 7/2020 | Hering et al. | | |
| 2020/0230313 A1 | 7/2020 | Mojarrad et al. | | |
| 2020/0238004 A1 | 7/2020 | McCullough | | |
| 2020/0254172 A1 | 8/2020 | Forster et al. | | |
| 2020/0254185 A1 | 8/2020 | Bar-el et al. | | |
| 2020/0261643 A1 | 8/2020 | Boyaval et al. | | |
| 2020/0261648 A1 | 8/2020 | Groszmann et al. | | |
| 2020/0261657 A1 | 8/2020 | Gibson et al. | | |
| 2020/0289745 A1 | 9/2020 | Harris et al. | | |
| 2020/0297927 A1 | 9/2020 | Conrath et al. | | |
| 2020/0315918 A1 | 10/2020 | Naygauz | | |
| 2020/0322793 A1 | 10/2020 | Yang | | |
| 2020/0338271 A1 | 10/2020 | Harris et al. | | |

(56) References Cited

U.S. PATENT DOCUMENTS

2020/0345927 A1* 11/2020 Hessam ................ A61M 5/172
2020/0345929 A1   11/2020 Ben-David et al.
2021/0228799 A1    7/2021 Streit et al.

FOREIGN PATENT DOCUMENTS

| WO | 2018183039 A1 | 10/2018 |
| WO | 2018226565 A1 | 12/2018 |
| WO | 2019018169 A1 | 1/2019  |
| WO | 2019022950 A1 | 1/2019  |
| WO | 2019022951 A1 | 1/2019  |
| WO | 2019032101 A1 | 2/2019  |
| WO | 2019143753 A1 | 7/2019  |

OTHER PUBLICATIONS

Omnipod Grip Shield Designed by Deck My Diabetes; Amazon. Available for sale Dec. 14, 2020 https://www.amazon.com/Deck-My-Diabetes-Flexible-Additional/dp/B08QL3TVZB/ref=sr_1_6?keywords=insulin+pump+overlay&qid=1639074568&sr=8-6 (Year: 2020).

RightCare CGM Adhesive Universal Overpatches; Amazon available for sale May 6, 2020. https://www.amazon.com/Adhesive-Universal-Covered-Synthetic-Extreme/dp/B083QMYXQ7/ref=sr_1_27?keywords=overpatch&qid=163080153&sr=8-27&th=1 (Year: 2020).

* cited by examiner

DEFORMABLE DRUG RESERVOIR FOR WEARABLE DRUG DELIVERY DEVICE

CROSS-REFERENCE TO RELATED APPLICATIONS

This application is a division of U.S. patent application Ser. No. 17/246,116, filed Apr. 30, 2021, the contents of which are hereby incorporated by reference herein.

BACKGROUND

Field of the Disclosure

The present disclosure relates to drug delivery devices. More particularly, the present disclosure relates to deformable drug reservoirs for delivery devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, the size and the profile of the device can be greatly improved. By decreasing the height and/or profile of the drug reservoir, the size and the profile of the device can be reduced. The lower and more compact profile can provide a more comfortable device for the user and reduce instances of devices being caught on clothing, preventing accidental leakage from the device.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug delivery device comprises a housing, an adhesive pad associated with the lower surface of the housing and configured to removably attach to a human body surface, a deformable drug reservoir positioned within the housing and including an outlet, a needle fluidically connected to the drug reservoir and configured to define at least a portion of a fluid flow path between the drug reservoir and said human body surface. The drug delivery device also includes a controller configured to control the components of the drug delivery device to execute a drug delivery routine and a delivery assembly associated with the drug reservoir and including a roller and a drive assembly, wherein the drive assembly is configured to move the roller from a first position to a second position so as to cause the roller to contact and deform the reservoir, thereby conveying a drug from the reservoir via the outlet during a drug delivery routine.

This and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
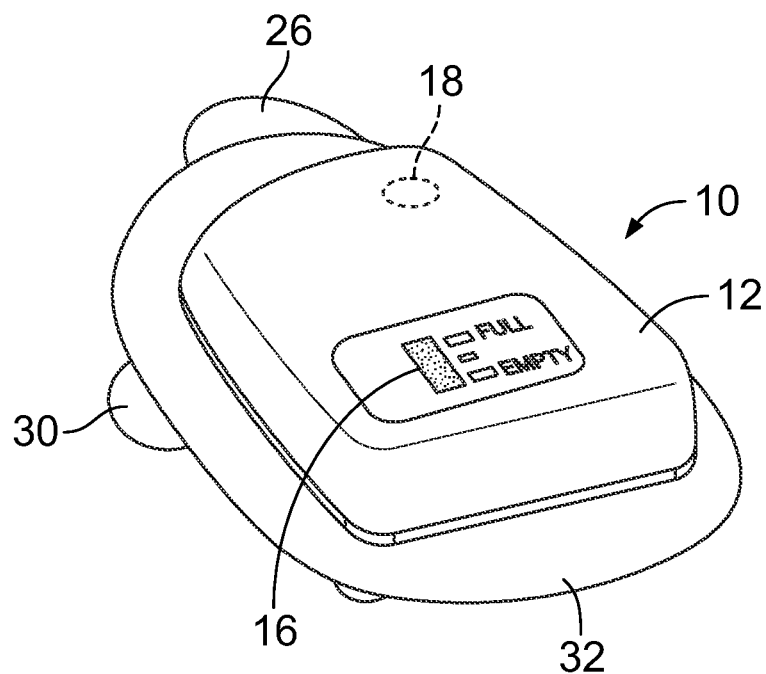
FIG. 1 is a top perspective view of a drug delivery device according to conventional design.
Figure 2:
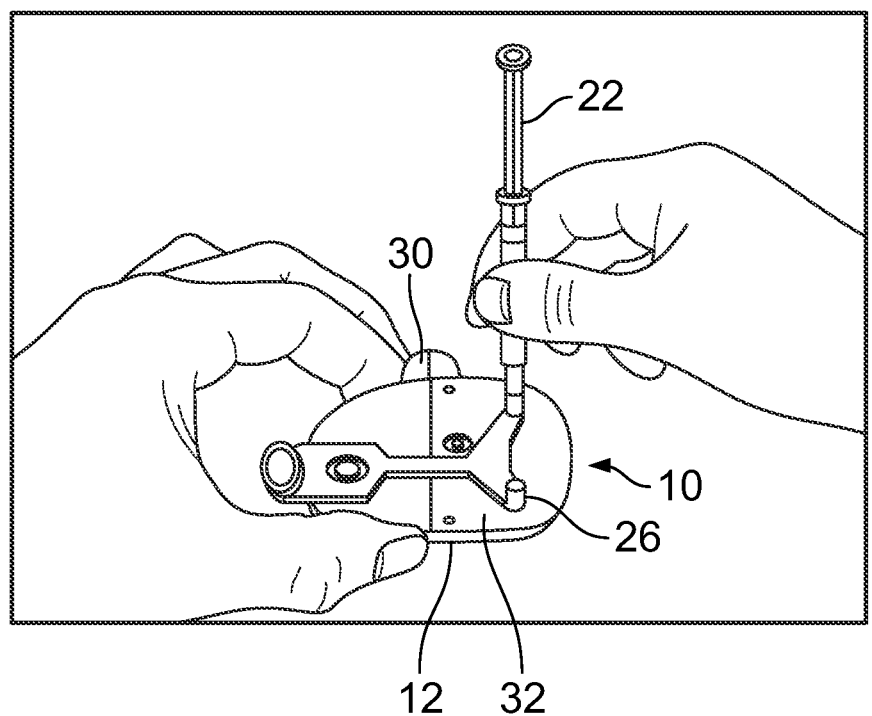
FIG. 2 is a bottom perspective view of the drug delivery device of FIG. 1.
Figure 3:
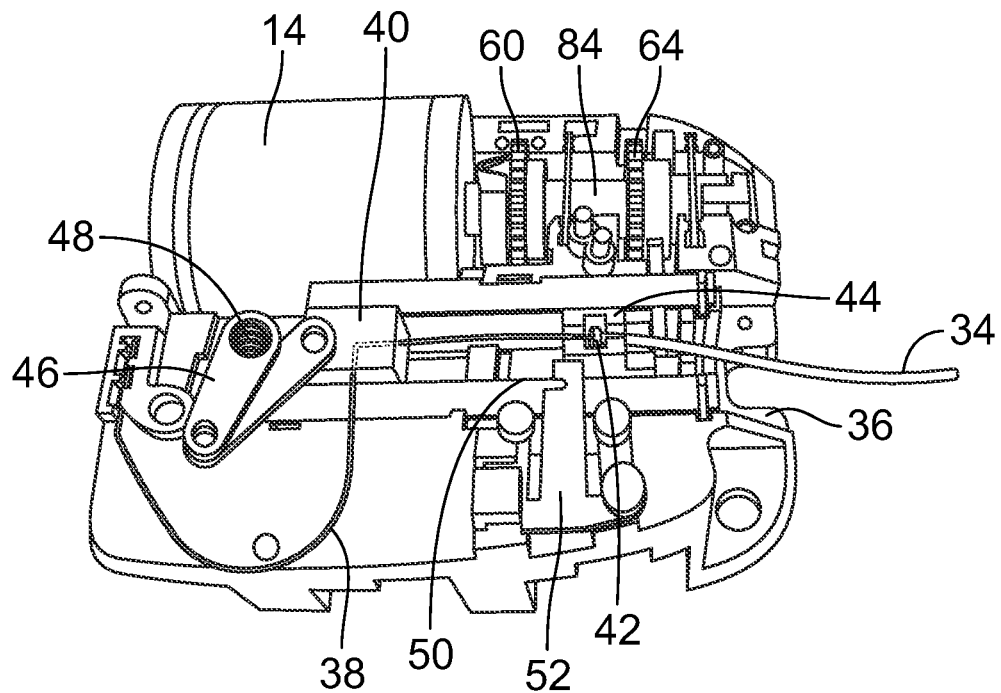
FIG. 3 is a top perspective view of the interior components of the drug delivery device of FIG. 1.
Figure 4:
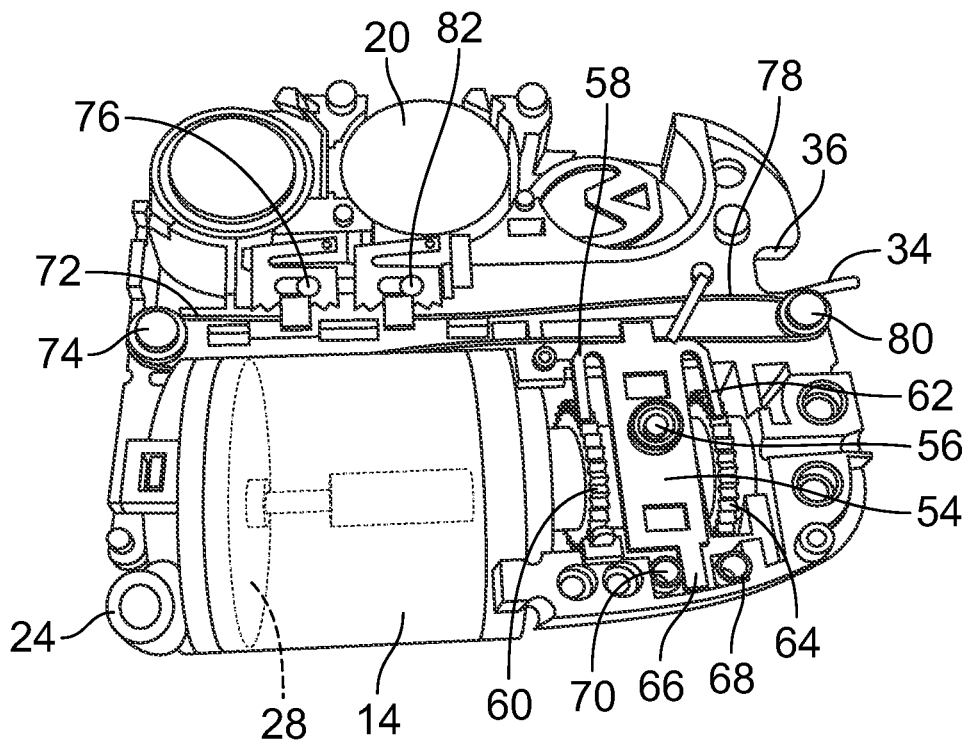
FIG. 4 is a bottom perspective view of the interior components of the drug delivery device of FIG. 1.
Figure 5:
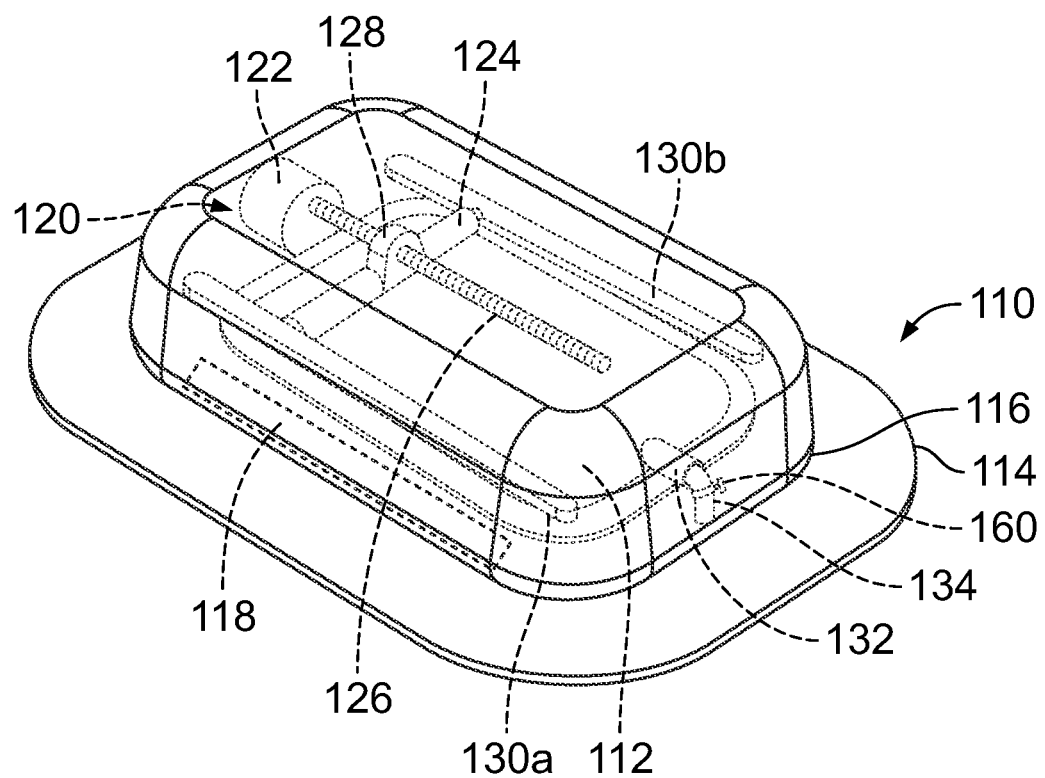
FIG. 5 is a top perspective view of an exemplary embodiment of a drug delivery device with an improved drug reservoir and drive assembly, according to an aspect of the present disclosure.
Figure 6:
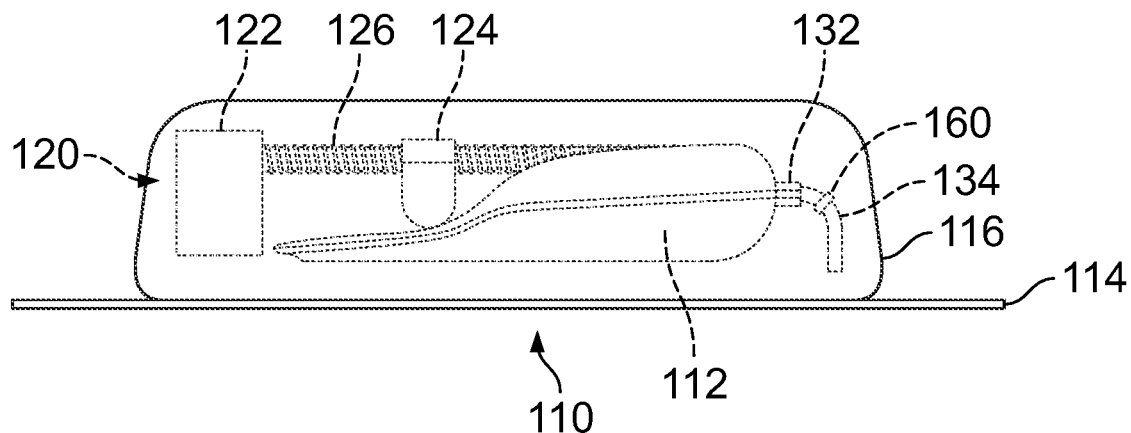
FIG. 6 is a side elevational view of the drug delivery device of FIG. 5.

FIGS. 5 and 6 show an exemplary drug delivery device 110 embodying aspects of the present disclosure. The drug delivery device 110 includes a housing 116. The housing 116 contains or encloses the functional components of the device 110, including a controller 118 and reservoir 112. The reservoir 112 is configured to be filled with a liquid drug to be delivered to a patient, with the reservoir 112 being filled either before or after the reservoir 112 is mounted within the housing 116, which may include the reservoir 112 being filled by a medical professional shortly before the device 110 is activated for a drug delivery routine. The methods and devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

The device 110 also includes a needle fluidically connected to the drug reservoir 112 and configured to define at least a portion of a fluid flow path between the drug reservoir 112 and a subject or patient. The needle and fluid flow path may be variously configured without departing from the scope of the present disclosure, with the needle and flow path being generally as described above with regard to the device of FIGS. 1-4 in an exemplary embodiment. The housing 116 has an adhesive pad 114 associated with its lower surface and configured to removably attach to a human body surface. The adhesive can be a pressure sensitive adhesive, particularly any medical grade pressure sensitive adhesive. The adhesive can be rubber, acrylic, and/or silicone based, for example.

The controller 118 is configured to control the components of the drug delivery device 110 to execute a drug delivery routine. The controller may include a microprocessor (which, in fact may include multiple physical and/or virtual processors) and one or more electrical circuits and memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessor to carry out one or more actions as described below.

The device 110 may also include at least one indicium associated with a display of the device. The indicium is configured to provide information to a user, which may include for example an indication that the device is ready to begin a drug delivery procedure, that the device is performing a drug delivery procedure, that the device has completed a drug delivery procedure, and/or that there has been an error. The indicium may display or represent the status of the device in any suitable manner. For example, in one embodiment, an indicium may be configured as a shortened message that can display different words, and it may include colors and/or lights to further indicate the state of the device. The indicium may utilize any other type of indication known in the art without departing from the scope of the present disclosure.

The controller 118 may be coupled (directly or indirectly connected) to the components of the device 110, such as the needle and display. The controller may operate each component, each of which may be an assembly of other devices or equipment, to execute a drug delivery routine. The controller may be programmed to perform other actions as well. Among the components coupled to the controller is a delivery assembly 120 configured to convey the drug from the drug reservoir via an outlet, as will be described in greater detail herein.

The device 110 can also include buttons or icons associated with the controller 118. The buttons or icons may be variously configured and positioned at any suitable location of the device. The device may include two buttons or icons, for example, with one button/icon being a start button/icon for initializing a procedure and the other button/icon of the set being a stop button/icon for stopping a procedure.

Unlike the rigid drug reservoir of the on-body delivery device of FIGS. 1-4, the drug reservoir 112 of FIGS. 5 and 6 is at least partially deformable and/or flexible. The drug reservoir can be any appropriate shape, being generally rectangular with curved or rounded corners in the illustrated embodiment. In an exemplary embodiment, the drug reservoir is configured as a large, flat, flexible bag formed of two films sealed together along at least one edge, and possibly all four edges, of the reservoir or a single film sealed along at least one edge. The reservoir may extend to occupy a significant portion of the length and width of the interior of the housing, which may be advantageous by decreasing the height of the reservoir without decreasing its capacity. For example, the reservoir (when filled with a drug) may have a height that is less than half the height of a conventional rigid reservoir (which may be in the range of about 6 mm to about 18 mm). By changing the size/shape of the reservoir from a traditional "syringe-style" reservoir with a round or oval cross-section (as employed in the device of FIGS. 1-4), the delivery device can be much lower profile, making it is less likely to be caught on clothing and/or dislodge, which can lead to leaking.

The drug reservoir 112 may be formed of any suitable material or combination of materials, along with being defined by a single layer or multiple layers of different materials. In an exemplary embodiment, the reservoir is formed of one or more film layers comprised of any one or more of a variety of materials, including thermoplastic materials and elastomers. Suitable materials can include (without limitation) polyethylene, polypropylene, polyurethanes, polyamides, polyesters, ethylene vinyl acetate, natural or synthetic polyisoprene, polybutadiene, polychloroprene, silicone, nitrile rubbers, nylon, olefin, and polyvinyl chloride. The film layer or layers can be comprised of blends or combinations of any of the preceding materials. Different layers of the film can be comprised of the same material or material combinations or different materials or material combinations.

The drug reservoir 112 includes at least one outlet 132, which may be located at, incorporated into, or otherwise associated with one edge of the drug reservoir 112. The outlet 132 includes an opening of the flexible reservoir and may also include a conduit 134, such as a tube or tubing that is sized to fit securely in the opening of the drug reservoir 112. If provided, the tube or tubing may be formed of any of a variety of materials, including being formed of a generally rigid material or combination of materials and being formed of a generally deformable or flexible material or combination of materials. By way of example, the conduit may be formed of a polymeric material, such as a plastic or rubber polymer, polyvinyl chloride, polyethylene, or a combination of these. The outlet and conduit define a portion of the fluid flow path from the drug reservoir to the needle of the drug delivery device.

The fluid flow path may also include a clamp or valve 160 associated with the conduit 134, which may be positioned at or adjacent to the outlet 132 of the drug reservoir 112. The valve or clamp 160, which may be variously configured without departing from the scope of the present disclosure, is configured to selectively allow and prevent fluid flow between the drug reservoir and the needle. In one embodiment, the clamp or valve 160 includes one or more clamps or valves configured to be automatically (i.e., non-manually) moved between closed and open conditions, such as by the controller 118. In the open condition, the clamp or valve 160 allows fluid flow through the conduit 134. In the closed condition, the clamp or valve 160 prevents fluid flow through the conduit 134. The manner in which the clamp or valve 160 prevents fluid flow through the conduit 134 may vary depending on the configurations of the clamp or valve 160 and the conduit 134. For example, in the embodiment shown in FIGS. 5 and 6, the conduit 134 is configured as a flexible tube, with the clamp or valve configured as a pinch valve, which may squeeze the conduit 134 to close it, thereby preventing fluid flow through the conduit 134. If the conduit 134 is differently configured (e.g., as a rigid tube), the clamp or valve may be differently configured (e.g., as a ball valve) to selectively allow and prevent fluid flow through the conduit 134. The valve may be configured as, but is not limited to, a glove valve, ball valve, check valve, gate valve, tilting disk check valve, swing-check or stop-check valve. It is also within the scope of the present disclosure for the valve to be configured as an electromechanical valve, such as a solenoid valve.

The drug is conveyed out of the device by operating a delivery assembly, which may be variously configured to move the drug from the reservoir via the outlet, with FIGS. 5-10 illustrating exemplary embodiments with different delivery assembly configurations. Similar components are numbered similarly throughout the Figures.

In general, the delivery assembly typically includes two components: a roller 124/224/324 and a drive assembly that is controlled by the controller to move the roller. The roller 124/224/324 includes one or more surfaces configured and oriented to contact the drug reservoir 112/212/312. The roller 124/224/324 may be configured to contact the drug reservoir 112/212/312 at any position into which the roller 124/224/324 may be placed or may instead be configured to move into at least one position in which it is not in contact with the drug reservoir 112/212/312. Movement of the roller corresponds to movement or release of the drug from the drug reservoir. The roller is at least movable from a first position to a second position, but may also be movable between the first and second positions. The first position of the roller may be located on, near or adjacent to a first end of the drug reservoir, such as the edge most distal to the outlet of the reservoir (which is the left end of the drug reservoir in the orientation of FIG. 6). The second position may be located on, near or adjacent to the opposite end of the drug reservoir, proximal to the outlet (which is at the right end of the drug reservoir in the orientation of FIG. 6) and between the outlet and the first position.

The drug reservoir may be full or at least substantially full when the roller is in the first position and empty or at least substantially empty when the roller is in the second position. The roller may substantially flatten the drug reservoir at the location where it contacts the drug reservoir, such that movement of the roller from the first position toward the second position will force the drug toward the outlet via a peristaltic action (which may be understood as being similar to squeezing toothpaste from a tube). It should be understood that the roller is not limited to movement from the first position to the second position, but may be moved to other positions, such as a third position between the first and second positions. This may include the roller being moved in increments from the first position toward the second position, with a predetermined amount of a drug being dispensed from the drug reservoir upon each incremental movement. Indeed, the roller may be moved into any position relative to the drug reservoir without departing from the scope of the present disclosure, with the controller and drive assembly being configured to stop movement of the roller in each and/or any of these positions.

In the illustrated embodiments, the roller 124/224/324 has a first and second end, extending transversely along and past the width of the drug reservoir and a substantial portion of the width of the housing 116/216/324. The roller 124/224/324 can be configured as an individual bar or wiper or a plurality of connected bars or wipers (for example) and be formed of a generally rigid or generally deformable or flexible material. As described above, the roller includes one or more surfaces configured to be at least partially positioned to contact and deform the drug reservoir, with it being advantageous for such a surface to be generally smooth or otherwise configured to be moved along the drug reservoir without puncturing the drug reservoir. Components and features of the roller (including any attachment mechanism by with the roller is associated to the drive assembly) may vary depending on the configuration of the associated drive assembly and drug reservoir, as should be clear from the description which follows.

Turning now to the drive assembly, it may be variously configured without departing from the scope of the present disclosure. Regardless of the configuration of the roller and drive assembly, it may be advantageous for the drive assembly to include one or more guide rails 130a/130b/230a/230b/330a/330b or a comparable mechanism configured to define the path along which the roller may be moved. In the illustrated embodiments, a pair of parallel guide rails 130/230/330 are linear or substantially linear and elongated, extending perpendicularly to the associated roller and defining a linear or substantially linear path for the roller. The guide rails may extend along at least a portion of the associated drug reservoir and be positioned at or near at least one lateral edge of the drug reservoir. In one embodiment, the guide rail or rails extend the full length of the drug reservoir. The first end of the guide rail or rails may correspond to the first position of the roller and the second end of the guide rail or rails may correspond to the second position of the roller. It should be understood that the illustrated guide rails and the paths they define are merely exemplary and that devices according to the present disclosure may employ guide rails that are differently configured and define different paths than what is shown.

The roller may be coupled to the associated guard rail or guard rails by any suitable approach. In an exemplary embodiment, each guide rail may include a channel or groove for receiving or accommodating a portion of the associated roller. The channel or groove may extend along the entire length of the guide rail or along just a portion of the length of the guard rail. In the illustrated embodiments, a first guide rail is configured to receive a first portion, such as the first end, of the roller and a second guide rail is configured to receive a second portion, such as the second end, of the roller.

Figure 7:
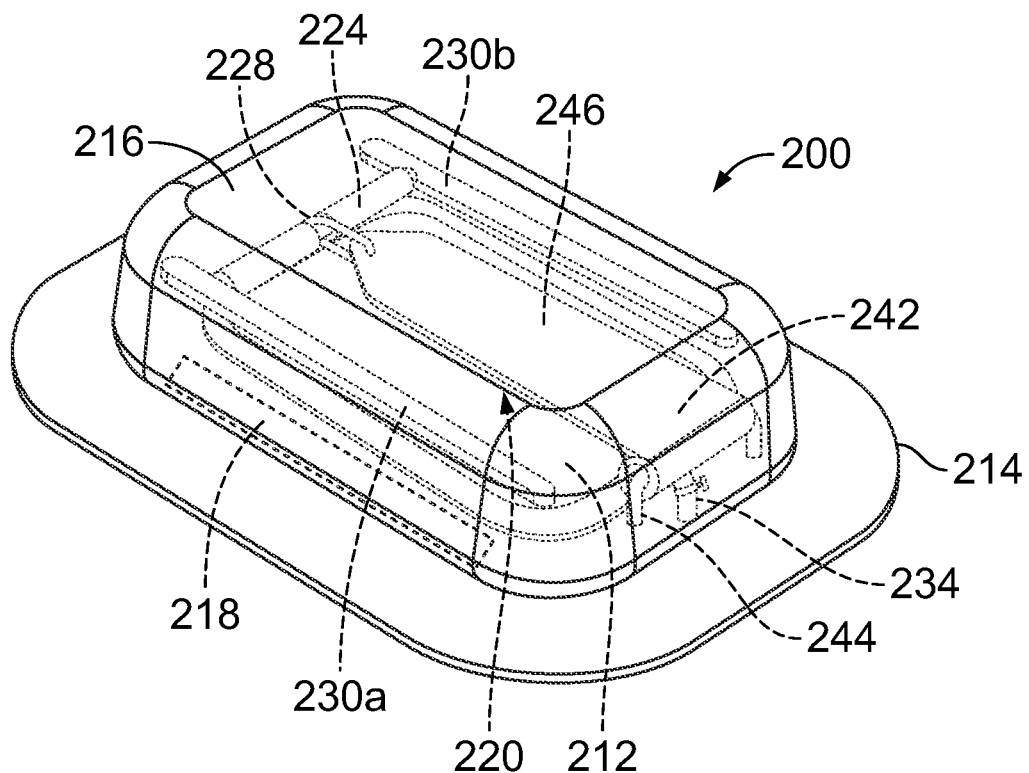
FIG. 7 is a top perspective view of a second exemplary embodiment of a drug delivery device with an improved drug reservoir and drive assembly, according to an aspect of the present disclosure.
Figure 8:
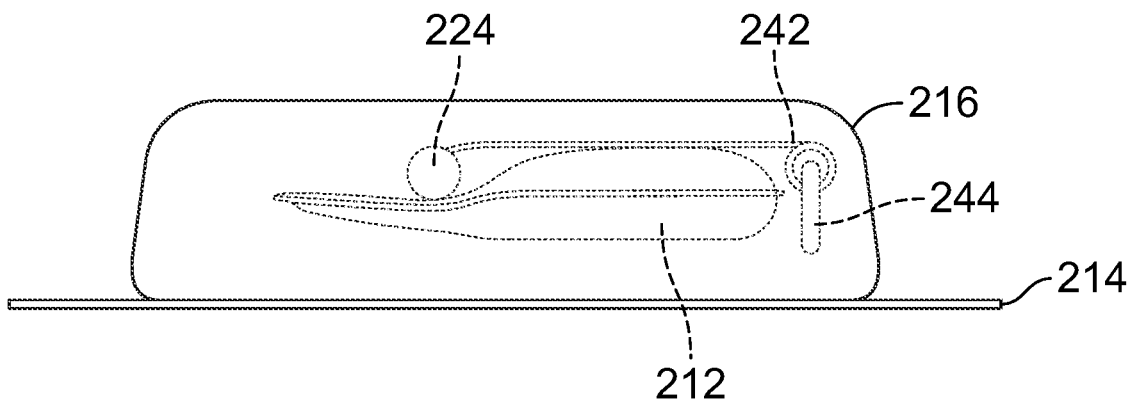
FIG. 8 is a side elevational view of the drug delivery device of FIG. 7.
Figure 9:
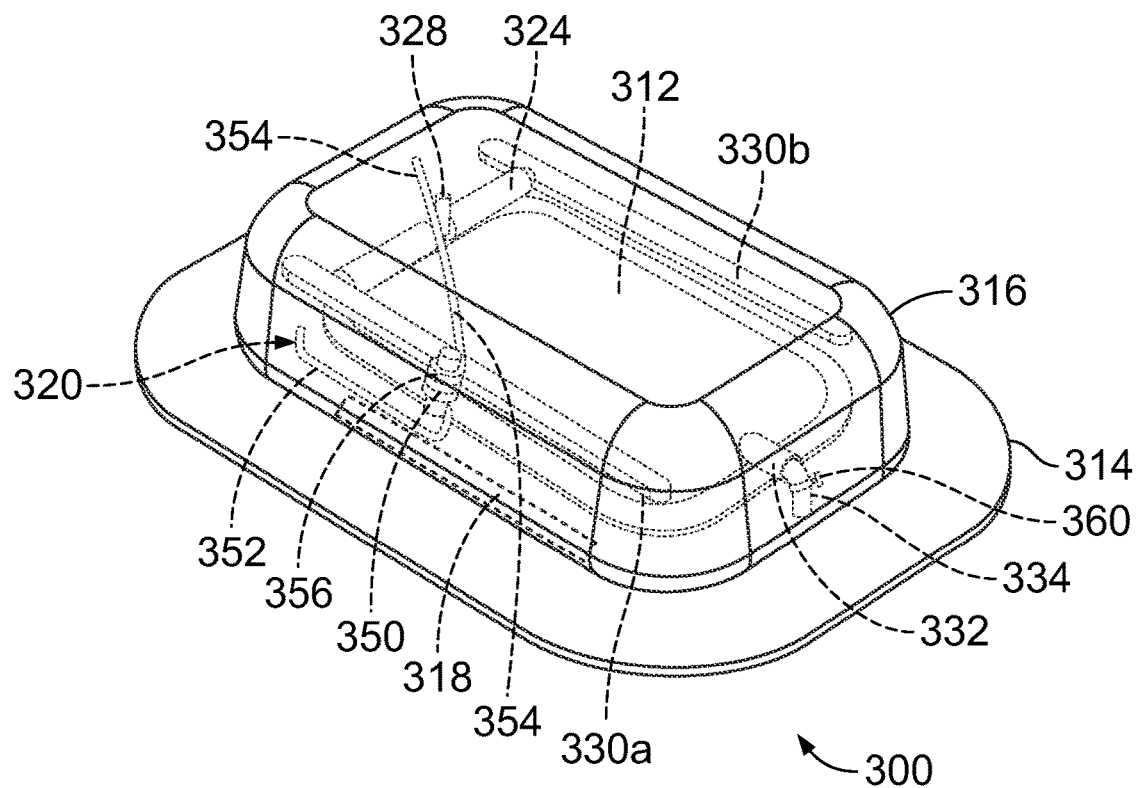
FIG. 9 is a top perspective view of a third embodiment of a drug delivery device with an improved drug reservoir and drive assembly, according to an aspect of the present disclosure.
Figure 10:
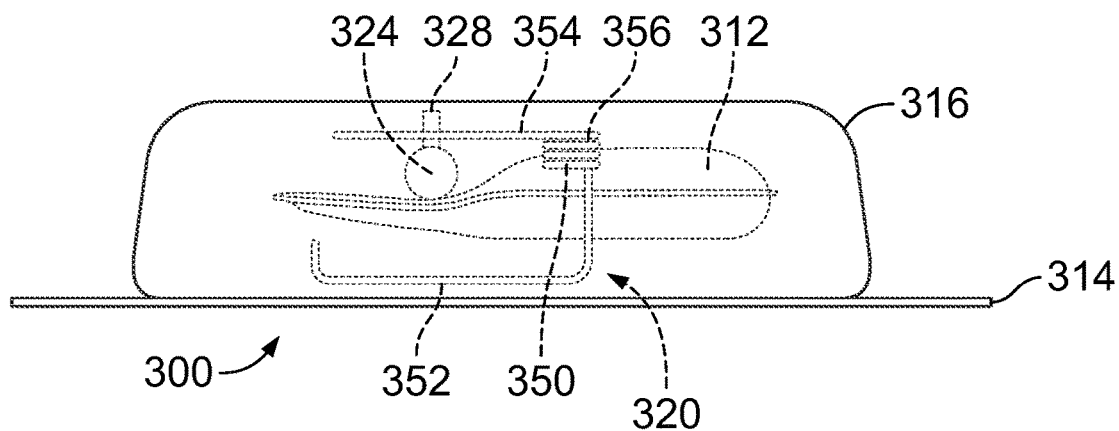
FIG. 10 is a side elevational view of the drug delivery device of FIG. 9.

The drive assembly of the delivery assembly that moves the roller along the guard rail or guard rails may be provided in a variety of configurations to impart different types of movement to the roller. Examples of these assemblies are shown in FIGS. 5-10, with the understanding that many differently configured assemblies may be employed to impart similar or different types of movement to the roller. FIGS. 5, 7, and 9 illustrate the top perspective views of the assemblies, while FIGS. 6, 8, and 10 illustrate side elevational views of each embodiment. Each of FIGS. 5, 7, and 9 show the roller at or near a first position of the roller, while FIGS. 6, 8, and 10 show the roller at an intermediate position between the first and second positions. For illustrative purposes, the guard rails are not illustrated in FIGS. 6, 8, and 10, being shown only in FIGS. 5, 7, and 9.

In one embodiment, the drive assembly may comprise a screw, which may be variously configured without departing from the present disclosure, such as being configured as a lead-screw, screw jack, ball screw, roller screw, or linear rail actuators (for example). The drive assembly of FIGS. 5 and 6 utilizes a lead-screw 126 and a motor 122 associated therewith and configured to rotate the lead-screw 126 about its central axis. The lead-screw may be externally threaded, while the roller 124 includes an internally threaded opening 128 which receives the lead-screw 126. In such an embodiment, the motor 122 is driven in a forward direction to rotate the lead-screw in a first direction (e.g., a clockwise direction) to move the roller in a first direction, such as in a direction from the first position toward the second position (i.e., toward the outlet 132 of the drug reservoir 112). Rotating the lead-screw in the reverse direction moves the roller 124 in an opposite second direction, such as in a direction from the second position toward the first position (i.e., away from the outlet 132 of the drug reservoir 112).

The lead-screw 126 and valve or clamp 160 may be coordinated by the controller 118 to work in concert, with the lead-screw 126 being prevented from rotating when the valve is in the closed condition and caused to rotate when the valve is in the open condition. Alternatively, the valve or clamp 160 may be configured to automatically open upon application of a sufficient amount of force, with the valve or clamp 160 being closed until the roller is moved. Once the roller is moved toward the second position, it will cause the drug to flow out of the drug reservoir via the outlet, applying sufficient force to the valve or clamp to cause it to open.

In another embodiment, the drive assembly may include at least one spring. The below embodiments illustrate the use of a constant force spring (FIGS. 7 and 8) and a torsion spring (FIGS. 9 and 10), but it is well within the teaching of the present disclosure to include other types of springs, which may include compression and extension springs, for example.

In the embodiment of FIGS. 7 and 8, the drive assembly 220 includes a constant force spring 242. The constant force spring 242 is comprised of a large, mostly flat piece 246 that is configured to wind around a spool 244 and can exhibit a consistent force over the range of its motion. The flat piece 246 may be a thin strip comprised of steel or another metal. The spring can be a spiral wound torsion spring, and it can also include an attachment ring 228 for connection to the roller 224.

The constant force spring 242 is configured to automatically move from an uncoiled condition to a coiled or partly coiled condition. As the spring is coiled, the attachment ring 228 pulls the roller from the first position toward a second position more proximate to the outlet, along the drug reservoir. The constant force application of the spring can be especially useful for constant or uniform flow of the drug from the reservoir 212. While the spring 242 is biased to move from the uncoiled condition toward a coiled condition, it should be understood that a mechanism may be provided to uncoil the spring 242, moving the roller in the opposite direction.

The constant force spring may be moved in coordination with the status of the valve 260. When the valve is in the closed position, the constant force spring may be prevented from moving from the uncoiled to the coiled condition and when the valve is in the open position the constant force spring may automatically move from the uncoiled to the coiled condition, moving the roller toward the second position and conveying the drug from the drug reservoir via the outlet.

The embodiment of FIGS. 9 and 10 includes a drive assembly 320 with a torsion spring 350. The torsion spring 350 is comprised of a coiled portion 356 and first and second ends 352 and 354. The spring 350 can be comprised of steel or other metal, for example. The second end 354 is in contact with a raised component 328 on the roller 324. The coiled portion is biased to move from a coiled condition toward an uncoiled or less coiled condition. When uncoiling, the second end 354 will apply a force to the raised component 328 on the roller 324. The force from the second end 354 will push the raised component and attached roller from a first position on the drug reservoir toward the second position (i.e., toward the outlet of the drug reservoir). It is also contemplated that a mechanism may be provided to move the spring 350 from a less coiled condition to a more coiled condition, thus moving the roller in the opposite direction.

The torsion spring may be moved in coordination with the status of the valve 360. When the valve 360 is in the closed position, the torsion spring may be prevented from moving from the coiled condition toward the uncoiled or less coiled condition. When the valve is in the open position, the torsion spring may automatically move from the coiled condition toward the uncoiled or less coiled condition, moving the roller along the drug reservoir and conveying the drug from the reservoir via the outlet.

It should be understood that the foregoing drive assemblies are merely exemplary and that other assemblies may be employed without departing from the scope of the present disclosure. It is also contemplated that a delivery assembly may include two or more differently configured drive assemblies to move the roller of the delivery assembly. This may include a first drive assembly configured to move the roller in a direction from the first position toward the second position and a second drive assembly configured to move the roller in a direction from the second position toward the first position. If multiple drive assemblies are provided, they may be similarly or differently configured. In any case, as described above, it should be understood that the roller will be moved by the drive assemblies based on signals from the controller, which may be based on the status of the device. This may include the controller controlling the drive assembly to move or change condition, the controller causing a valve or clamp to move or change condition (which allows the drive assembly to automatically move or change condition), or the controller causing both the drive assembly and the valve or clamp to move or change condition in order to cause the roller to move.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug delivery device comprising:
a housing;
an adhesive pad associated with a lower surface of the housing and configured to removably attach to a human body surface;
a deformable drug reservoir positioned within the housing and including an outlet;
a needle fluidically connected to the outlet of the drug reservoir and configured to define at least a portion of a fluid flow path between the drug reservoir and said human body surface;
a controller configured to execute a drug delivery routine; and
a delivery assembly associated with the drug reservoir and including a roller and a drive assembly, wherein the drive assembly includes a constant-force spring biased to move from an uncoiled condition toward a coiled condition, with movement of the constant-force spring from the uncoiled condition toward the coiled condition moving the roller from a first position to a second position so as to cause the roller to contact and deform the drug reservoir, thereby conveying a drug from the drug reservoir via the outlet during a drug delivery routine, wherein the constant-force spring is not wound around the roller.

2. The drug delivery device of claim 1, wherein
the drive assembly comprises an elongated guide rail extending between a first end of the guide rail and a second ends of the guide rail,
at least a portion of the roller is configured to move along the guide rail, and
movement of said at least a portion of the roller in a direction from the first end of the guide rail toward the second end of the guide rail corresponds to movement of the roller in a direction from said first position toward said second position.

3. The drug delivery device of claim 2, wherein the guide rail is substantially linear.

4. The drug delivery device of claim 2, wherein said at least a portion of the roller configured to move along the guide rail comprises a first end of the roller.

5. The drug delivery device of claim 1, wherein
the drive assembly comprises elongated first and second guide rails each extending between a first end of the guide rail and a second ends of the guide rail,
a first portion of the roller is configured to move along the first guide rail,
a second portion of the roller is configured to move along the second guide rail, and
movement of said first and second portions of the roller in a direction from the first end of the guide rails toward the second end of the guide rails corresponds to movement of the roller in a direction from said first position toward said second position.

6. The drug delivery device of claim 5, wherein the guide rails extend along opposite lateral edges of the drug reservoir.

7. The drug delivery device of claim 5, wherein the guide rails are substantially linear.

8. The drug delivery device of claim 5, wherein said first portion of the roller comprises a first end of the roller and said second portion of the roller comprises a second end of the roller.

9. The drug delivery device of claim 5, wherein
the guide rails extend along opposite lateral edges of the drug reservoir,
said first portion of the roller comprises a first end of the roller,
said second portion of the roller comprises a second end of the roller, and
at least a portion of the constant-force spring is positioned between the guide rails.

10. The drug delivery device of claim 5, wherein the guide rails are substantially linear and substantially parallel.

11. The drug delivery device of claim 1, further comprising a valve associated with the outlet and configured to be moved from a closed condition to an open condition, wherein
the constant-force spring is prevented from moving from the uncoiled condition to the coiled condition when the valve is in the closed condition, and
the constant-force spring is configured to automatically move from the uncoiled condition toward the coiled condition when the valve is in the open condition.

12. The drug delivery device of claim 1, wherein the second position is positioned between the outlet and the first position.

13. The drug delivery device of claim 1, wherein the drug reservoir is substantially full of the drug in the first position and substantially empty in the second position.

14. The drug delivery device of claim 1, wherein the roller is movable to a third position.

15. The drug delivery device of claim 14, wherein the third position is between the first and second positions.

16. The drug delivery device of claim 1, wherein the drive assembly is further configured to move the roller in a direction from the second position toward the first position.

17. The drug delivery device of claim 1, configured to deliver a drug comprising pegfilgrastim.

18. The drug delivery device of claim 1, wherein the delivery assembly is configured to move the constant-force spring in a direction from the second condition toward the first condition.

19. A drug delivery device comprising:
a housing;
an adhesive pad associated with a lower surface of the housing and configured to removably attach to a human body surface;
a deformable drug reservoir positioned within the housing and including an outlet;
a needle fluidically connected to the outlet of the drug reservoir and configured to define at least a portion of a fluid flow path between the drug reservoir and said human body surface;
a controller configured to execute a drug delivery routine; and
a delivery assembly associated with the drug reservoir and including a roller and a drive assembly, wherein the drive assembly includes a constant-force spring biased to move from an uncoiled condition toward a coiled condition, with movement of the constant-force spring from the uncoiled condition toward the coiled condition moving the roller from a first position to a second position so as to cause the roller to contact and deform the drug reservoir, thereby conveying a drug from the drug reservoir via the outlet during a drug delivery routine, wherein the constant-force spring is wound onto a spool that is spaced from the roller.

\* \* \* \* \*